United States Patent [19]

Alkaitis et al.

[11] 4,162,986
[45] Jul. 31, 1979

[54] OIL-SOLUBLE HIGH METAL CONTENT TRANSITIONAL METAL ORGANIC OXY, HYDROXY, COMPLEXES

[75] Inventors: Anthony Alkaitis, Cleveland Heights; Paul L. Cells, Cleveland, both of Ohio

[73] Assignee: Mooney Chemicals, Inc., Cleveland, Ohio

[21] Appl. No.: 881,363

[22] Filed: Feb. 27, 1978

Related U.S. Application Data

[63] Continuation-in-part of Ser. No. 808,407, Jun. 20, 1977, abandoned.

[51] Int. Cl.$^2$ .................. C10M 1/40; C10M 1/24; C10L 1/32; B21B 45/02
[52] U.S. Cl. .................................. 252/33.2; 44/51; 72/42; 252/35; 252/36; 252/37.7; 252/400 R; 252/430
[58] Field of Search .............. 252/33.2, 35, 36, 37.7, 252/430, 400 R; 44/51; 72/42

[56] References Cited

U.S. PATENT DOCUMENTS

| | | | |
|---|---|---|---|
| 2,320,392 | 6/1943 | White | 252/33.2 |
| 2,322,307 | 6/1943 | Neely et al. | 252/33.2 |
| 2,367,470 | 1/1945 | Neely et al. | 252/33.2 |
| 2,417,428 | 3/1947 | McLennan | 252/33.2 |
| 2,616,904 | 11/1952 | Asseff et al. | 252/33.2 |
| 3,714,042 | 1/1973 | Greenough | 252/33.2 |

Primary Examiner—Delbert E. Gantz
Assistant Examiner—Irving Vaughn
Attorney, Agent, or Firm—Maky, Renner, Otto & Boisselle

[57] ABSTRACT

Metallo-organic compositions soluble in oils and hydrocarbon solvents, of a high transitional metal content and highly overbased character, are prepared from sources of transitional metals (or of transitional in conjunction with nontransitional metals) reacted with mixed organic acids comprising at least one monocarboxylic acid and a second acid, either a sulfonic acid or a different molecular weight monocarboxylic acid. Formation of the complexes requires the use of excesses of metal over acids, and the use of an oxygen-supplying material such as air, regardless of whether the metal source be a free metal, an oxide or a hydroxide. Alkoxyalkanols or glycols may be used in addition to the required acids.

These compositions comprise (1) a polynuclear core of a normally insoluble metal oxide or hydroxide which is crystalline by X-ray and electron diffraction observation, with metal hydroxyl carboxylate groups (and when present, sulfonate or alkoxyalkanol or glycol groups) ionically and hydrogen bonded to the core element atoms, and additional acid groups having an unbound association with a core and its bonded groups; (2) ultimate particles having structure with minimum average undissociated molecular weight of about $10^4$; and (3) a ratio of total moles of metal to total moles of organic acid moieties being greater than 1 to 1.

30 Claims, No Drawings

OIL-SOLUBLE HIGH METAL CONTENT TRANSITIONAL METAL ORGANIC OXY, HYDROXY, COMPLEXES

CROSS-REFERENCE TO RELATED APPLICATION

This application is a continuation-in-part of our pending application Ser. No. 808,407, filed June 20, 1977 now abandoned.

BACKGROUND OF THE INVENTION

Many types and mixtures of metal salts and soaps of natural or synthetic organic acids, particularly carboxylic acids, have been suggested and commercially offered over several decades. These have been used to supply metals in forms which are soluble in organic liquids, especially in various hydrocarbon oils and solvents, to form solutions having various desired properties and uses. For example such metal containing solutions may be useful as catalysts such as in fuels or in paints, varnishes and other film forming compositions. Many of these salts and soaps also have been useful as lubricant additives where high solvent solubility has not been of such importance.

Desire for economy in the production of such materials or for improved product quality has led to several variations in methods of producing the metal soap compounds by the classical double decomposition reaction and, as exemplified by Olson U.S. Pat. No. 2,753,049, by direct metal reaction.

As various organic carboxylic acids have become available in commercial quantities, either from new natural sources, or as synthetic acids or standardized synthetic acid mixtures, the possibility of using these to produce metallic salts or soaps has been motivated, for example, by a lower price; by a relative uniformity of the commercial acids; or by a better color, or at times the non-colored, characteristics of the salt products; by higher solubility of the salt products in various solvents in other components of ultimate products for which the metal salt is to be used; or stability in storage of the metal compositions or of their solutions. Prior art salt or soap compositions contain one mole of a carboxylate group per equivalent of metal present and they generally have a resinous, non-crystalline structure further characterized by a usual absence of any hydroxyl groups.

Other more complex metal organic compositions also have been investigated and marketed. Examples of the complex compositions are found in, for example, Rinse U.S. Pat. No. 3,518,287 or Collins et al U.S. Pat. No. 3,941,606.

High metal content with retention of high solubility has been sought, at times to minimize introduction of material other than catalytically active metal atoms, for example, into a process or product environment, to reduce raw material cost or to minimize weight or volume of the metal composition thereby reducing required storage space, packaging costs, or freight and other shipping costs.

Hence considerable attention has been given in the prior art to the production of the so-called overbased metal soaps or compositions, that is, compositions having greater than one-to-one ratios of metal-to-acid equivalents, for example, the Piotrowski et al U.S. Pat. Nos. 3,827,979 (by a carbonation process); Le Suer et al 3,312,618; Asseff et al 2,616,904; 2,616,905; Norman et al 2,595,790; Murphy 3,725,441; and patents cited in these. The preparation of oil-soluble metal soaps of various metals and acids and mixtures of acids, including some basic lead soaps is described in U.S. Pat. No. 2,584,041. Water is required in the process and the presence of air is optional.

SUMMARY OF THE DISCLOSURE

This invention relates to oil-soluble and hydrocarbon-soluble, highly overbased transition metal-organic compositions comprising a metal oxide-hydroxide-carboxylate complex wherein the metal content which comprises at least one metal which is a transitional metal is in chemical combination partly with oxygen in a polynuclear metal oxide crystallite core and partly with at least two different monocarboxylic acids or a mixture of one or more monocarboxylic and monosulfonic acids containing at least two carbon atoms as hydroxyl-metal-carboxylate and hydroxyl-metal-sulfonate groups, at least one of the acids being a monocarboxylic acid containing at least seven carbon atoms, and when the second acid is also a monocarboxylic acid, the second acid contains a number of carbon atoms in its longest chain differing by at least two carbon atoms from the total number of carbon atoms in the other, at least a portion of the carboxylate and sulfonate groups being hydrogen bonded to oxygen atoms of the core, and the remainder of the carboxylate and sulfonate groups are unbonded and in equilibrium with the bonded groups, and the ratio of total metal moles to the total moles of organic acid is greater than one.

The invention also relates to the methods of preparing the highly overbased transition metal-organic compositions of the invention.

DESCRIPTION OF THE PREFERRED EMBODIMENTS

The present invention is concerned with a new class of transitional metal organic compositions with metal-to-acid mole ratios somewhat greater than 1 to 1 and generally greater than 2 to 1. These compositions are soluble in aromatic and aliphatic hydrocarbon solvents, especially mineral spirits and light oil, and also in drying oils, despite the very high transitional metal content. The compositions of the invention characteristically include, in chemical combination with at least one transitional metal, at least two different organic acid moieties selected from unsaturated and, with some metals to avoid unwanted side reactions preferably saturated, aliphatic or alicyclic monocarboxylic acids and oil-soluble sulfonic acids; at least a first one being a monocarboxylic acid moiety. The first acid should have at least seven carbon atoms. Although there is no critical upper limit on the number of carbon atoms, 22 carbon atoms is a practical upper limit.

There is no carbon chain restriction on the second acid except that when the second acid is a carboxylic acid, the longest carbon chain in the second carboxylic acid should differ from the first acid by at least two carbon atoms. There is no restriction in carbon chain length imposed on any third organic acid employed as a ligand, nor on any additional acids thus employed. The third or additional organic acid may be a monocarboxylic or a dicarboxylic acid. Examples of dicarboxylic acids which are useful include malonic acid, succinic acid, adipic acid, glutaric acid, pimelic acid, azelaic acid, etc. While one or more of the acids may be volatile low molecular weight types, combinations of non-volatile acids which follow the above rules, may also be employed.

The compositions appear from molecular weight determinations to be polymers, which may be designated as metal oxide- or hydroxide-oxy acylate (i.e. carboxylate) or sulfonate complexes, or where moieties of aliphatic ether alcohols are included in the compositions, as metal oxide and hydroxide-carboxylate-alkoxide complexes. The complexes appear to be higher in molecular weight than the prior art soaps of the same metals.

From X-ray diffraction studies of solids and solutions, and electron diffraction and microscopy study of solids, it appears that, in the solid solvent-free compositions of the invention, the ultimate particles each comprise a metallo-oxy or metallo-oxy-hydroxy crystallite core, surrounded by an amorphous matrix of organic ligand groups. These groups include bound groups attached through ionic and hydrogen bonding to the atoms of the core crystallite especially at its surface, and absorbed unbound organic groups. These complexes may also be termed heterogeneous in respect to such crystalline and non-crystalline structure within the ultimate particles, and as well with respect to the matrix, inasmuch as different organic moieties are involved.

The particle size distribution peak is relatively narrow. For a particular choice of metal and acids, variation in the metal to acid ratio seems generally to change the proportion of crystallite-cored particles, rather than their size.

The crystal core phases have been found to be $Mn_3O_4$ (spinel), CoO (cubic), $Fe_3O_4$ (spinel) and CuO (triclinic) for specimens containing respectively only manganese, cobalt, iron and copper. Where two different metals are used for the preparations, even with the second being non-transitional, atoms of the second metal are found to be present in the core. When, for example, a cobalt source is included with a manganese source in what would be otherwise normally a preparation of a manganese complex with a spinel type core, the cobalt appears to replace part of the four-fold coordinated manganese in the spinel arrangement.

It may be here observed that when the transitional metal source is an oxide, the core crystalline phase contains a metal oxide portion in which the metal valence is higher than the source oxide.

When only carboxylic acids or carboxylic acid moiety sources (acids, esters) are used in the preparation, it is believed that the organic moiety or ligand species is present as a soap-like metal carboxylate-hydroxide component, R—$CO_2$—M—OH, where the R group is a carbon chain from the acid and M is the transition metal. Such components engender soap-like characteristics in these compositions. From infrared investigations, it appears that the organic moiety attachment occurs especially through hydrogen bonding between the hydroxyl on the organic moiety and oxygen atoms on the surface of the crystal core, though ionic bonding to the core atoms appears also to occur. An absorption type equilibrium is established between the core with bound organic species and the unbound organic species which are associated with the core.

The amorphous character of the matrix, resulting from the dissimilarity of the acid moieties, is believed to confer high solubility in aromatic and aliphatic hydrocarbons (such as xylene and mineral spirits) and for some compositions to the extent of solution metal contents exceeding 50% by weight.

Each individual crystallite, considered for simplicity of discussion as a cube, is about 50 to 100Å on a side. The crystal unit cell is approximately 10Å on a side, and contains about 20 metal oxide or metal hydroxide molecules. The specific number of molecules, specific unit cell size, and crystal composition depends on the particular metal in question. Thus one manganese type crystal with a 100Å edge contains about 1,000 unit cells or 20,000 metal molecules, or with a 50Å edge, about 125 unit cells or 2,500 metal molecules. The crystal face in a 100Å edge core contains about 600 active sites for organic moiety attachment by hydrogen bonding, which may account for the unusual stability of the complexes.

In the solvent-free or solid complex compositions of the individual metals, manganese, cobalt, iron and copper and mixed metals such as manganese-cobalt, manganese-zinc and manganese-barium, the ultimate particle sizes run about 50 to 100Å on the edge, with a minimum average molecular weight of about $10^4$. However, when the molecular weight determinations are made by vapor pressure or freezing point depression methods, the apparent molecular weights are considerably smaller in many of the solvents used, (e.g., carbon tetrachloride running about from 500 to 1,000), since the number of large weight particles (comprising crystallite cores with retained bound organic moieties) is far outnumbered by unbound organic moiety fragments which become dissociated in solution from their respective original cored particles.

The complexes of this invention also are characterized as amorphous aggregates of crystalline-cored particles which arise due to the affinity of one complex particle for another. A typical aggregate or cluster size, of 200–500Å on a side varying for different metals, may represent a cluster of up to about 250 individual crystals. In solutions, the aggregate size on the one hand, or the degree of dissociation on the other, is a function of the solvent, the temperature, and the solution concentration.

The degree of association of these complexes thus varies in different solvents such as carbon tetrachloride, benzene, trichlorobenzene and cyclohexane. In dissociating solvents, such as carbon tetrachloride, the degree of association in comparison to prior art metal soaps averages about five. In any solvent, a near integral multiple value is usually encountered.

A typical crystal of this type of composition would be representable by the empirical formula,

$$[(ML_a)_b\text{-}(HO\text{-}M\text{-}R_1)_c\text{-}(HO\text{-}M\text{-}R_2)_d]_f,$$

wherein

M is a metal atom with valence greater than one, is a transitional metal in the majority of metal occurrences in the composition, and each M may represent different metals;

L is an oxygen or a hydroxyl group;

$R_1$ is an organic monocarboxylate group;

$R_2$ is an organic monocarboxylate or monosulfonate group;

a is from about one to two;

b is greater than one;

c and d are each greater than zero, and c+d is at least three; and f is at least one.

Ether alcohols or polyols may be used in addition to the acid sources or in place of a part of the $R_2$-containing ligand.

In addition to usefulness based on known applications of the contained metals, or on the high metal content with retained solubility in hydrocarbons, or on relatively low toxicity for some metal types as compared with other high metal content organic compositions, various of these new compositions exhibit also efficacies for equal metal content exceeding prior soluble metal compositions, or new utilities.

The major application of these complexes will be as catalysts for a variety of chemical operations in which prior art metal soaps currently are used. The use of the complexes results in certain advantages in addition to the high metal content. The complexes are not only soluble in organic media, but they also exhibit some of the important properties of the metal oxides used in heterogeneous catalysts. Consequently, they will be useful in bridging the gap between heterogeneous and homogeneous catalysts by supplying advantages common to each.

While metal alkoxide oligomers, including bimetallic types, have been known and exhibit similar properties, novel metal oxy hydroxy acylate ologimers can be produced more easily, at lower cost, and with greater heterogeneity as complexes of the present invention.

The manganese, cobalt, iron, copper and nickel high metal content complexes are useful as catalysts for many chemical reactions, either directly as homogeneous catalysts or in preparation of heterogeneous catalysts. They can be used an anti-knock agents for gasoline, fuel additive type combustion improvers, smoke or toxic fume suppressants, unsaturated polyester cure promoters, driers, and ultra violet co-catalysts for inks and coatings. The iron, and to a lesser degree, the manganese and cobalt complexes are useful in preparation of catalysts for gasification of primary fuels.

As oxidation or polymerization catalysts, the complexes are useful, for example as curing agents for floor covering mastics; curing agents (especially the iron and cobalt types) for core binders; and catalysts in the restricted oxidation reaction for production of sulfur from sour gas, in the sour gas wet process with absorption agents for precipitation of sulfur.

A further application is as retention aids for volatile toxic substances, for which they may serve as oil-carried scavengers in scrubbers; as scavengers for various oxides of nitrogen; in systems treating combustion products of power plants; and extracting toxic constituents from ashes.

The manganese, cobalt, iron and copper complexes find use in surface preparation for adhesives for promoting bonding to various surfaces, and the copper and cobalt types are valuable as catalysts for improving rubber adhesion.

Other applications of the complexes of the invention are as agents for ultraviolet screeners (manganese, cobalt, iron, copper); as micronutrient sources (manganese, cobalt, iron, copper); as lubricant additives, (manganese, cobalt); and as wire drawing lubricants.

The characteristic high metal content (with hydrocarbon solubility) makes these complexes useful also in manufacture of glass coatings affording tinting and infrared screening areas, since they will decompose cleanly to the oxide state; for metallizing; for baked-on refractory high-temperature coatings and adhesives; and for high-temperature refractory surface resistance coatings, and other conductive coatings.

The manganese, cobalt, and iron type compositions (some of which are photosensitive), show a high degree of magnetic susceptibility from which follows utility for manufacture of tapes for magnetic recoding devices, and of particulates used in magnetic or electrostatic printing; and for preparation of liquid and dry toners, and of charge control agents for electrostatic printing.

The copper complexes are useful active components in fungicides, anti-fouling paints for marine use, and stabilizers for sulfur compounds.

To prepare the overbased metal complexes, a reaction is initiated with heating if necessary between a previously formed, or formed-in-situ, divalent transitional metal carboxylate and a predetermined excess of divalent transitional metal hydroxide formed-in-situ from the metal or its lower oxide in the presence of an oxygen-supplying material such as air. Usually mineral spirits is a convenient diluent or reaction medium. The reaction end point is reached when the soluble metal content of the reaction mass reaches a maximum. Generally there will be little or no unreacted residues at this stage if the reactant amounts are carefully formulated, but any unreacted metallic residues can be removed by filtration.

For many purposes, the reaction product is left in solution in the reaction medium as a solvent, and the product solution may then be adjusted to the desired concentration by distilling off excess reaction medium or by solvent addition. Fairly mobile solutions have been obtained containing more than 50% metal by weight.

The metal contained in the overbased complexes of the invention must be at least in part a transitional metal. When the complexes contain additional metals, any desirable metal can be utilized such as calcium, barium, zinc, etc. Of the transitional metals, copper and those elements found in the first transition series, namely, scandium, titanium, vanadium, chromium, manganese, iron, cobalt and nickel are preferred.

Although specific details will vary, each transition metal complex is prepared by a similar general method. When a metal oxide such as manganese oxide is used, it is slurried with an excess of water and with what, by ordinary stoichiometric considerations, would be a deficiency of organic acids at a selected mole ratio of metal-to-acid, agitated, and heated at the reflux temperature until no further reaction occurs, and the "excess" metal oxide has been completely converted to hydroxide. The batch is heated to about 120°–149° C. (300° F.) or higher, until the free water is eliminated. Air is introduced into the mix at 110°–150° C. until insoluble manganous hydroxide has been solubilized by conversion into the complex. Previously bound water which is freed during air or oxygen blowing may be removed during the blowing step. Appearance and metal content analysis determination indicate when processing can be terminated.

If manganese metal is employed rather than manganese oxide, some air may be introduced to facilitate the formation of manganous oxide or hydroxide in the first step, but under some control to avoid a too large excess, which would result in formation of some insoluble higher oxides together with manganese hydroxide. A similar process is used with cobalt, nickel and iron metals. Either copper metal or cuprous oxide may be employed to form the copper complex, but in both instances, air is required for oxidation.

The mole ratio of total metal or metals to total acids which characterizes specific complexes can be found by determining the metal content of the complex and comparing it stoichiometrically to the quantity of reactant acids used in the synthesis of the complex. The metal content can be determined by complexometric titration procedures or other conventional methods.

Various mixtures or formulations of reactant monobasic organic acids may be used to facilitate processing or for collateral reasons. Examples of organic carboxylic acids useful in the invention include propionic acid, butyric acid, 2-ethylhexoic acid, commercially available standardized nonanoic acid, neodecanoic acid, oleic acid, stearic acid, naphthenic acids, tall oil acid, and other natural and synthetic acids and acid mixtures.

The sulfonic acids include the aliphatic and the aromatic sulfonic acids. They are illustrated by petroleum sulfonic acids or the acids obtained by treating an alkylated aromatic hydrocarbon with a sulfonating agent, e.g., chlorosulfonic acid, sulfur trioxide, oleum, sulfuric acid, or sulfur dioxide and chlorine. The sulfonic acids obtained by sulfonating alkylated benzenes, naphthylenes, phenol, phenol sulfide, or diphenyl oxide are especially useful.

Specific examples of the sulfonic acids are dodecylbenzene sulfonic acid, didodecylbenzene sulfonic acid, dinonylbenzene sulfonic acid, octadecyldiphenyl ether sulfonic acid, bis-cetylphenyl disulfide sulfonic acid, cetoxy-caprylbenzene sulfonic acid, dilauryl beta-naphthalene sulfonic acid, the sulfonic acid derived by the treatment of polyisobutene having a molecular weight of 1500 with chlorosulfonic acid, paraffin wax sulfonic acid, cetyl-cyclopentane sulfonic acid, lauryl-cyclohexane sulfonic acid, and polyethylene (molecular weight of 750) sulfonic acid, etc.

When attempts are made to prepare overbased products by the procedure of the invention but using only one acid, it appears that the use of the single acid limits the metal-to-acid mole ratio to about 0.75. In this context, "single acid" comprehends, for example, such an isomeric mixture as commercial neodecanoic acid where a variety of isomers are present though of substantially uniform molecular weight for the entire composition, and also even a single narrow cut of naphthenic acids, where there occur acid molecules of diverse structure and some difference in molecular weights, or tall oil acids with saturation differences.

In the initial reaction batch, other materials may be used for various ancillary purposes, for example, to serve as dispersing agents or to produce dispersing agents for other reactants. Hydrazine can be included to reduce especially manganese initially present in higher than the manganous state. Polyols or alkoxyalkanols can be added as promoters or to reduce a viscosity of the reactive mixture. Acids such as formic, acetic or hydrochloric acid can be included as promoters.

There may be employed according to conventional practice, viscosity modifiers such as glycols, alcohol ethers or glycol ethers, amines, phosphate esters, etc. However, higher metal-to-acid ratios may be attained with use of alcohol- or glycol-ethers. Also anti-oxidants may be employed if desired, such as the "Eastazone" listed in some of the Examples below.

Some ancillary constituents may react and combine with the metal, but the net effect is not deleterious to the process or ultimate product. For example, alkoxyalkanols of higher molecular weight and boiling ranges may become a combined organic moiety in the final product.

Several examples of the mixed organic acid salt complexes and the method of preparation are presented below in tabular listings giving for each example: (a) the raw materials and amounts used; (b) for the solution product usually brought to 1,000 gram final batch weight, (i) the weight percent metal content after removal of any unreacted or insoluble metal or oxide, (ii) the total metal-to-total acid molar ratio ("M/A"), (iii) the weight percent conversion of the metal available in the source, and in some examples, (iv) other properties such as percent by weight of non-volatile material ("non-volatiles" or "N.V.") which is the presumed active complex in the solution product; and (c) for the "active component", that is the solid obtained upon removing the diluent or solvent, the metal content by weight percent.

The percentages referred to in the tables and elsewhere are weight percentages, unless otherwise stated. The molar ratio and conversion values are equally pertinent or applicable to the solution product and to the isolated active component, which is found to have a complex constitution, of the nature previously described.

The actual reaction product amount in the product solution is determinable by evaporation of the solvent and any ancillary material such as Cellosolve by heating the product solution to constant weight as in a standard NVM ("non-volatile material") determination procedure.

For the raw material under each example heading, excepting Example 5, given in pounds, in column "Bt" there are given for each batch component the amount used in grams for a thousand grams of the batch solution product obtained with the designated metal content; and, for certain components in the column "Moles" or "Eq", respectively the gram-moles, or the gram-equivalent based upon apparent molecular weight, as given by chemical analysis. Thus the amounts stated represent the active content of the designated components or, in the case of the "princpal" organic acids which are technical or standardized mixtures, the gram-mole or grams-equivalent figure is based upon the determined acid number for the nominal raw material acid.

For ammonium hydroxide, hydrochloric acid and hydrazine hydrate, the amounts stated are weights used respectively of the usual concentrated ammonia, 37% acid and 35% hydrazine water solutions. The mineral spirits used have a boiling range of about 149° to 205° C. The amounts of air given in cubic feet (taken at ambient conditions, without reduction to standard or dry conditions) are the total amounts blown by the time of oxidation completion.

MANGANESE COMPLEXES

The manganese complexes generally are prepared as follows. A mixture of manganese metal, or any acid-soluble divalent manganese compound, but preferably manganous oxide, water and the selected acids in mineral spirits or other diluent medium is agitated in preferably an inert atmosphere such as nitrogen with heating as required to initiate an exothermic reaction and until completion of a first stage reaction resulting in a homogeneous, opaque, light tan, viscous, usually paste-like first stage product or intermediate. When manganese metal is used as the source of manganese rather than manganese oxide, some air is introduced to facilitate the formation of manganous oxide or hydroxide, but not enough air to lead to the formation of insoluble higher oxides or hydroxides. The first stage reaction intermediate or product is oxidized with heating by introducing gaseous oxygen, for example, by air blowing.

Though the dehydration may also be carried on during the aforegoing steps, preferably the first stage product is itself substantially dehydrated before oxidation, usually by heating the batch above 100° C., with the nitrogen gas blanket being maintained.

The progress of the first stage is followed by some form of analytic control with periodic sampling of the batch. For example, a sample of the reaction mixture can be centrifuged or filtered and the color of the lighter precipitate examined for the color of residual greenish manganous oxide or black manganese metal powder. Actual chemical analysis of the liquid (supernatant in the centrifuge tube or the filtrate) for dissolved manganese until a constant maximum of manganese content in successive samples also indicates substantial completion of the first stage reaction.

When it is determined that the first stage of the reaction has been completed, it is desirable to remove any free water present in the reaction mixture. The term free water refers to any water present which is not chemically bound to the first stage reaction product. The free water is removed by heating the reaction mixture to a temperature above 100° C. and maintaining this temperature until dehydration is completed.

In the third stage of the reaction the batch temperature is raised to about 140° C. or higher and air is bubbled into the reaction mass. In some instances the air is preheated to about 150° C. It is preferred that the air blowing for the third stage should not be begun without first completing the second stage product dehydration. Some bound water is freed during the oxidation stage, and this is removed during oxidation. During this oxidation, the viscosity of the batch and its turbid opacity are reduced progressively to result ultimately in a dark brown transparent reaction product solution form.

The third stage blowing is continued with heating until there is substantially no further water or immiscible phase being distilled over into the separator, and until the reaction batch reaches the uniform dark brown or the manganese content becomes constant in the filtrate of periodically taken batch samples. Due to impurities in technical grade reactants, or compromise with optimum process conditions, the crude liquid product may require clarification as by filtration while hot, with a filter aid. Mineral spirits washings of the filter cake are added to the filtrate.

The liquid product may be diluted to a lower concentration by mineral spirits or other solvent. Advantageously, the product may be vacuum distilled to a higher concentration containing as much as 75-80% solids. Of course, where it is known that filtration of the resulting concentrated solution will not be unacceptably slowed down, solvent may be distilled from the product in the reaction vessel.

Moreover, it generally is possible, by removing all solvent and other volatile constituents or components from the batch to obtain a substantially anhydrous, usually brittle, solid product. Products have been thus obtained with manganese contents in excess of 60%.

It has been noted that when the usual manganese liquid product is diluted with solvents and treated with aqueous hydrochloric acid, there develops a green color usually characteristic of the trivalent manganese ion. Thereafter, upon heating in air, the thus-treated product generally becomes colorless which indicates the manganese ion is being reduced. This is consistent with the known instability or easy reduction of trivalent manganese ion.

By the preferred process and process conditions, a very high manganese recovery, that is, conversion of the manganese to the soluble product form generally has been readily obtained exceeding 95% and frequently 99%.

As a manganese source, the metal is usually less desirable than a manganous compound, especially manganous oxide, because under the more acceptable and readily maintained process conditions, with the metal as the source, some inactive manganese by-products are formed, probably higher oxides or hydrated oxides of manganese. This results in a slight reduction of the conversion, i.e., yield of soluble manganese in the product.

In certain instances with manganese metal where air has been introduced at an early stage in the overall operation and before completion of what has been here termed the "first stage", appreciable solids are observed after the third stage oxidation step is deemed completed, the crude batch product filters slowly, and the conversion of manganese is reduced. However, after settling for several hours, the crude batch product is readily filterable. After the unreacted manganese or insoluble manganese components are removed, the product is acceptable as an overbased composition for many purposes.

Process-wise with respect to manganese, it is important that an appreciable amount of water be present during the first stage reaction, especially with metallic manganese as the manganese source. Also the oxidation by air blowing in the third stage reaction preferably should be carried out with heating in the latter part of the process.

Broadly, it may be stated that at atmospheric pressure, the first reaction stage, for which in practical sense the presence of water is required, is to be conducted below 100° C., and the second and third stages above 100° C. More specifically temperature ranges of about 60° to about 120° C. are useful for the first stage, and temperatures of from about 100° to about 160° C. for the second and third stages.

In the manganese examples reported below in Tables I-III, the process usually is carried out under reflux conditions in the first stage until dehydration or water removal begins. The batch heating generally is begun as materials are added. Where used, the hydrazine hydrate and hydrochloric acid are added mainly after the manganese source.

For the first stage in these examples, (apart from Example 4 using metallic manganese noted below, and the comparative Example 1 with 7¼ hours total for the first stage, of which 1½ hours are below 126° C., and 5¼ hours at temperatures from 126° to 154° C.), the times required are about 4½ to 5½ hours below 100° C., followed by a period of about 2 to 4 hours at about 100° C. to dehydrate before introducing air.

For a third or oxidation stage, 4 to 5 hours of air blowing is required in Examples 2-4, 7-8, at 129° to 142° C.; in Example 1, about 3¼ hours between 147°-154° C.; but in Example 6 about 7¾ hours of which 5½ hours are between 131° C. and 146° C., after 2 hours between 110°-128° C.

In Example 4 after 12 hours for the nominal first stage and dehydration, the final air oxidation requires about 1½ hours at 138° C.

In Example 5 (batch quantities in pounds) the first stage requires about 5¼ hours with ¼ for bringing the batch to 99° C. and the balance of time at 90°–99° C. Without prior dehydration and interruptions of heating, the batch requires about 36 hours of air blowing at temperatures varying considerably but mainly in the range of 123°–148° C. Air blowing is begun at 89° C. as the temperature is being raised.

Particularly noteworthy for process comparison are the low solution product manganese content (6.23%), low metal-to-acid molar ration (0.92) or equivalent ratio (1.84) and hence basicity (84%) of the product solution and the low manganese conversion (13%) of Example 1 where water is not used (except for a trace contributed by the hydrazine solution) for the first stage of the process, as compared with Example 2, using water, and other examples with notable amounts (e.g. 9 to 21 gram mols) of water. Although otherwise the charge is about the same (in total equivalents of the same acids but in somewhat differing acid ratios, and with like amounts of manganese), the solution product of Example 2 contains 39.4% manganese and has a metal-to-acid molar ratio of about 5.73 or equivalent ratio or 11.7, 1070% basicity, and 96.5% conversion. Also the content of manganese in the solid active component obtainable from the respective product solutions are quite different, 38.8% and 50.8%. The effect of the water in Example 2, or conversely of the lack of water in Example 1, is evident particularly in view of slow first stage reaction even at 124° C. and long hold above 150° C. for completion and second stage dehydration before oxidation, as contrasted with the milder process conditions for the first stage in Example 2 and others as noted above.

TABLE I

| RAW MATERIAL | Ex. 1 Bt. | Moles | Ex. 2 Bt. | Moles | Ex. 3 Bt. | Moles | Ex. 4 Bt. | Moles | Ex. 5 Bt. | Moles | Ex. 6 Bt. | Moles |
|---|---|---|---|---|---|---|---|---|---|---|---|---|
| 2-ethylhexoic acid | 0 | — | 0 | — | 0 | — | 0 | — | 18 | 0.125 | 27 | 0.188 |
| neodecanoic acid | 106 | 0.56 | 117 | 0.62 | 117 | 0.62 | 162 | 0.87 | 136 | 0.727 | 94 | 0.500 |
| propionic acid | 41 | 0.55 | 23 | 0.31 | 23 | 0.31 | 63 | 0.85 | 18 | 0.243 | 18 | 0.189 |
| dodecylbenzene sulfonic acid | 26 | 0.08 | 0 | — | 0 | — | 39 | 0.12 | 42 | 0.126 | 56 | 0.167 |
| stearic acid | 11 | 0.04 | 89 | 0.32 | 89 | 0.32 | 16 | 0.06 | 0 | 0 | 18 | 0.064 |
| tall oil FA | 0 | — | 0 | — | 0 | — | 0 | — | 0 | — | 18 | 0.062 |
| tall oil | 0 | — | 0 | — | 0 | — | 0 | — | 0 | — | 18 | 0.060 |
| total organic acids | 184 | 1.23 | 229 | 1.25 | 229 | 1.25 | 280 | 1.90 | 214 | 1.22 | 249 | 1.23 |
| Cellosolve | 0 | — | 0 | — | 0 | — | | | 19 | — | 246 | 2.73 |
| hydrochloric acid | 0 | — | 0 | — | 5 | — | — | — | 6 | — | 7 | — |
| mineral spirits | 760 | — | 392 | — | 369 | — | 414 | — | 467 | — | 206 | — |
| water | 0 | — | 165 | — | 165 | — | 193 | — | 300 | — | 378 | — |
| 35% hydrazine | 2.5 | — | 0 | — | 2.1 | — | 11 | — | 0.7 | — | 12 | — |
| manganous oxide | 531 | 7.44 | 531 | 7.44 | 531 | 7.44 | — | — | 512 | 7.17 | 527 | 7.38 |
| manganese powder | — | — | — | — | — | — | 473 | 8.6 | — | — | 0 | — |
| air - total cu. ft. | 4.6 | | 7.1 | | 5.9 | | 6.2 | | yes | | 12.1 | |
| PRODUCT | | | | | | | | | | | | |
| % Mn | 6.23 | | 39.4 | | 40.3 | | 40 | | 39.4 | | 40.4 | |
| M/A ratio (molar) | 0.92 | | 5.73 | | 5.86 | | 3.83 | | 5.87 | | 5.9 | |
| Mn conversion % | 13.1 | | 96.5 | | 98.5 | | 85 | | — | | 98.5 | |
| % Non-volatile | 16.1 | | 77.5 | | 79.2 | | 77.4 | | 72 | | 79.0 | |
| ACTIVE COMPONENT | | | | | | | | | | | | |
| % Mn | 38.8 | | 50.8 | | 50.8 | | 51.7 | | 54.7 | | 51.1 | |

TABLE II

| RAW MATERIAL | Ex. 7 Bt. | Moles | Ex. 8 Bt. | Moles | Ex. 9 Bt. | Moles | Ex. 10 Bt. | Moles |
|---|---|---|---|---|---|---|---|---|
| 2-ethylhexoic acid | 0 | — | 0 | — | 130 | 0.90 | — | — |
| neodecanoic acid | 61 | 0.35 | 71 | 0.38 | — | — | — | — |
| propionic acid | 28 | 0.38 | 17 | 0.23 | — | — | — | — |
| dodecylbenzene sulfonic acid | — | — | — | — | — | — | — | — |
| stearic acid | 42 | 0.15 | 45 | 0.16 | 28.5 | 0.10 | — | — |
| tall oil FA | 0 | — | 0 | — | 0 | — | 0 | — |
| other | 0 | — | 0 | — | — | — | 340[1] | 1.0 |
| total organic acids | 131 | 0.88 | 132 | 0.77 | 158.5 | 1.00 | 340 | 1.0 |
| Cellosolve | 0 | — | 300 | — | (46 | 0.40)[2] | (48 | 0.42)[2] |
| hydrochloric acid | 8 | — | 8 | — | — | — | — | — |
| mineral spirits | 516 | — | 394 | — | 1800 | — | 1500 | — |
| water | 188 | — | 199 | — | 240 | — | 240 | — |
| 35% hydrazine | 12 | — | 13 | — | 8 | — | 8 | — |
| manganous oxide | 602 | 8.44 | 639 | 8.95 | 642 | 9.1 | 642 | 9.1 |
| manganese powder | — | — | — | — | — | — | — | — |
| air - total cu. ft. | 6.4 | | 7.6 | | 10 | | 9.5 | — |

1. Naphthenic acid bottoms      2. diacetone alcohol

| PRODUCT | | | | | | | | |
|---|---|---|---|---|---|---|---|---|
| % Mn | | 44.7 | | 48.9 | | 39.5 | | 39.5 |
| M/A ration (molar) | | 9.25 | | 11.55 | | 8.7 | | 8.6 |
| Mn conversion % | | 96 | | 99.2 | | 96.1 | | — |
| % Non-volatile | | 76.7 | | 79.7 | | 65.4 | | 82.4 |

TABLE II-continued

| | Ex. 7 | | Ex. 8 | | Ex. 9 | | Ex. 10 | |
|---|---|---|---|---|---|---|---|---|
| RAW MATERIAL | Bt. | Moles | Bt. | Moles | Bt. | Moles | Bt. | Moles |
| ACTIVE COMPONENT | | | | | | | | |
| % Mn | | | | 58.2 | | 61.3 | | 60.0 | — |

TABLE III

| | Ex. 11 | | Ex. 12 | | Ex. 13 | | Ex. 14 | |
|---|---|---|---|---|---|---|---|---|
| RAW MATERIAL | Bt. | Moles | Bt. | Moles | Bt. | Moles | Bt. | Moles |
| neodecanoic acid | 41 | 0.225 | 57 | 0.313 | 54 | 0.296 | 22 | 0.121 |
| propionic acid | — | — | 38 | 0.514 | — | — | — | — |
| stearic acid | 64 | 0.225 | 58 | 0.204 | 85 | 0.299 | 36 | 0.127 |
| butyric acid | 27 | 0.300 | — | — | 36 | 0.400 | 32 | 0.356 |
| other organic acids | — | — | — | — | — | — | — | — |
| total organic acids | — | 0.75 | 153 | 1.031 | 175 | 0.995 | 90 | 0.604 |
| Cellosolve | 180 | 2.0 | — | — | 180 | 2.00 | 300 | 3.33 |
| hydrochloric acid | — | — | 8 | — | — | — | — | — |
| mineral spirits | 1200 | — | 1100 | — | 1200 | — | 1300 | — |
| water | 210 | — | 200 | — | 210 | — | 200 | — |
| 35% hydrazine | 4.8 | — | 13 | — | 4.8 | — | 3.2 | — |
| Eastozone | — | — | — | — | — | — | — | — |
| manganese oxide | 642 | 9.06 | 642 | 9.06 | 642 | 9.06 | 642 | 9.06 |
| air - total cu. ft. | 7.7 | — | yes | — | yes | — | yes | — |
| PRODUCT | | | | | | | | |
| Mn % | | 40.3 | | 40.1 | | 40.6 | | 40.5 |
| M/A ration - moles | | 12.1 | | 8.8 | | 9.1 | | 15.0 |
| Mn conversion % | | — | | — | | — | | — |
| Non-volatile % | | 67.4 | | — | | — | | — |
| ACTIVE COMPONENT | | | | | | | | |
| Mn % | | | | 59.8 | | 59.2 | | 57.2 |

The metal-to-acid mole ratios obtainable in the manganese organic complex products, immediately apparent from the tables, are remarkably high in view of the hydrocarbon solubility evidenced by the metal content of the liquid products. Also notable is Example 10 where without other organic acids, naphthenic acid "bottoms" reactant, of wide composition and molecular weight range is used, thus imparting the required plural acid diversity or hetrogeneity.

The ultimate particles of the products of Examples 2–14 appear, by electron microscopy and diffraction on solid manganese complex product, and by X-ray diffraction on solid and solution products, each to be constituted of a polynuclear metal oxide, distorted spinel ($Mn_3O_4$) crystalline core of about 50 to 100Å edge size, which core is surrounded or encapsulated by a matrix of amorphous organic ligand material. From other considerations especially infrared investigations, the amorphous organic matrix is comprised of manganese-containing organic groups, typically as metal carboxylate groupings, or more particularly metal hydroxyl carboxylate groupings. Some of the organic groupings are retained by ionic and hydrogen bonding especially at crystallite face oxygen sites, and some absorptively. In the solid, amorphous clusters of these encapsulated structures occur up to about 300Å size. By freezing point depressions of non-associative solvents such as carbon tetrachloride, the average molecular weight for these manganese complexes typically appears to be 900±100, about five times that of analogous soaps.

Also by freezing point depression by the manganese compositions in associative solvents such as benzene and cyclohexane, average molecular weights of about 15,000 to 20,000 are observed. By gel permeation chromatography in tetrahydrofuran (THF), the average molecular weight of manganese complexes is on an order greater than 105, and in carbon tetrachloride, the "molecule" sizes are from 100 to 1,000Å. The largest fragment derived by heating for mass spectrum measurements represents a molecular weight of about 1,000. Vapor pressure depression measurements in carbon tetrachloride give average molecular weights of 6910±690.

As to other properties and characteristics, the manganese complexes show strong UV absorption in the 320–205 millimicron band, and manganese is present in the divalent and trivalent states. Magnetic susceptibility ($10^{-6}$ emu/g; room temperature) is usually about 51 for the manganese, as compared with 50 for the cobalt, 8640 for the iron and 4.8 for the copper complexes described below.

EXAMPLES—OTHER METALS

Using at least two different acids in the batch, chosen by the principles discussed above and with air blowing for oxidation, highly overbased compositions have been prepared with other transition metals using similar apparatus, though with some modifications of method. Table IV summarizes the Examples containing cobalt and copper.

TABLE IV

| | Ex. | Co-1 | Ex. | Co-2 | Ex. | Co-3 | Ex. | Cu-1 | Ex. | Cu-2 |
|---|---|---|---|---|---|---|---|---|---|---|
| RAW MATERIAL | Bt. | moles | Bt. | Moles | Bt. | Moles | Bt. | Moles | Bt. | moles |
| 2-ethylhexoic acid | — | — | — | — | 185 | 1.275 | — | — | — | — |
| neodecanoic acid | 108 | 0.60 | 180 | 1.0 | — | — | 77 | 0.4 | 54 | 0.30 |
| propionic acid | 56 | 0.75 | 60 | 0.8 | — | — | — | — | — | — |
| stearic acid | 43 | 0.15 | 58 | 0.2 | 64 | 0.225 | 29 | 0.1 | 43 | 0.15 |
| butyric acid | — | — | — | — | — | — | 44 | 0.5 | 36 | 0.40 |

TABLE IV-continued

| RAW MATERIAL | Ex. Co-1 Bt. | Co-1 moles | Ex. Co-2 Bt. | Co-2 Moles | Ex. Co-3 Bt. | Co-3 Moles | Ex. Cu-1 Bt. | Cu-1 Moles | Ex. Cu-2 Bt. | Cu-2 moles |
|---|---|---|---|---|---|---|---|---|---|---|
| amyl ac. phosphate | — | — | — | — | — | — | — | — | 19 | 0.15 |
| other org. acids | — | — | — | — | — | — | — | — | — | — |
| total org. acids | 207 | 1.50 | 298 | 2.0 | 229 | 1.50 | 150 | 1.0 | 152 | 1.0 |
| Cellosolve | 135 | 1.5 | — | — | 180 | 2.00 | — | — | — | — |
| mineral spirits | 1600 | — | 1700 | — | 1800 | — | 1700 | — | 1700 | — |
| water | 200 | — | 150 | — | 200 | — | 150 | — | 200 | — |
| Eastazone | — | — | 4 | — | 4 | — | 35 | — | — | — |
| triethanolamine | 15 | — | — | — | 15 | — | 25 | — | 25 | — |
| NH₄OH | 90 | — | 120 | — | 135 | — | 60 | — | 60 | — |
| amyl alc. mix. isom. | — | — | — | — | — | — | 15 | — | 45 | — |
| metal or oxi-e | 665* | 11.3 | 600* | 10.2 | 765* | 13.0 | 470** | 3.28 | 470** | 3.28 |
| air - tot. cu. ft. | 36 | — | 80 | — | 94 | — | 15 | — | 46 | — |
|  | *Co powder | | | | | | **Cu₂O | | | |
| PRODUCT | | | | | | | | | | |
| Metal % | 36.3 | | 35.9 | | 40.2 | | 35.98 | | 36.3 | |
| M/A ratio-moles | 5.49 | | 5.2 | | 3.2 | | — | | 5.65 | |
| Met. conversion % | 36.5 | | 51.0 | | 37.0 | | — | | — | |
| Non-volatile % | 76.96 | | 79.3 | | 86.6 | | 62.7 | | 61.2 | |
| ACTIVE COMPONENT | | | | | | | | | | |
| Metal % | 47.2% Co | | 45.2% Co | | 46.4 Co | | 57.4% Cu | | 59.3% Cu | |

Colbalt Examples (Table IV) IV)

With air introduction from the start, the mixture of Example Co-1 having considerable excess cobalt metal powder is heated to and held at about 70°–80° C., under total water reflux. During this heating, the reaction mixture is in two liquid phases and becomes quite viscous. In addition to the water initially charged and formed in the reaction, water is added to replace any carried off by the air and not condensed for reflux. Additions of mineral spirits also are made as needed to maintain fluidity. When the soluble cobalt content of the batch becomes substantially constant after about 9.5 hours of reaction, a further reaction with insoluble cobalt materials is promoted by an increase in temperature.

The temperature is raised slowly to about 154° C. while nitrogen is bubbled therethrough resulting in a large increase in soluble cobalt content and dehydration of the product. After about seven hours at the increased temperature, the reaction is complete. The unreacted excess metal is removed by filtration, resulting in 2335 g of a clear product solution containing 9.88% cobalt.

After further distillation of mineral spirits to a cobalt concentration of 36.33%, the final product is a clear, dark-brown mineral spirit solution of the complex. At 1% cobalt metal content, the solubility in mineral spirits is good.

The preparation of Example Co-2 using the same three acids is similarly carried out, with the primary differences in this example from Co-1 being omission of Cellosolve and of triethanolamine. Early in the dehydration stage, the mixture changes from blue to greenish. The first and second stages run about 13½ hours each.

A dark-brown product solution (1956 g) containing 12.44% cobalt is obtained, which combined with the washings of the filter cake represents 306 g of cobalt reacted. A clear dark-brown final liquid product is obtained upon concentration to 35.9% cobalt. This is a notably high cobalt content and the mineral spirits solubility is retained.

In Example Co-3, only two acids are used, 2-ethylhexoic and stearic acids, and 283 g of the cobalt reacts. The procedure again generally follows that used for Co-1 with 400 g of the mineral spirits total being added in later periods of dehydration. Again good solubility in mineral spirits, at high and low ranges of complex-content is observed despite the high metal content.

For the solid state, as in manganese compositions, ultimate particles comprise a cubic crystallite-core (here of CoO oxide type) encapsulated with some amorphous material, evidently metal hydroxyl carboxylate groupings with bound and unbound —OH. In carbon tetrachloride, freezing point depression indicate average molecular weight on the order of 500+100; by gel permeation chromatography, molecular sizes of 100 to 1,000Å and larger are observed. In the solids, the particle core size is again on the order of about 50 to 100Å, with amorphous clusters of about 300–400Å.

Copper Examples (Table IV)

In Example Cu-1, where the metal source is a stoichiometric amount of cuprous oxide, the three-acid mixture is heated to and held in the range of 71°–78° C. for 11 hours with continued introduction of air and total water reflux with further additions of water. The batch during further reaction after disappearance of the oxide is a single phase thin solution. The batch is heated to and held at about 150° C. for 4 hours to remove water. Nitrogen is bubbled through the mixture. The product solution is filtered, and then concentrated by removing mineral spirits to a brown liquid product of 35.98% copper content and a 57.4% copper content in the solid. Other properties are listed in Table IV.

The four-acid mixture of Example Cu-2 reacted by a procedure quite similar to that of Example Cu-1 results in a final liquid product containing 36.3% copper, and 61.2% N.V. solids with 59.3% copper.

Again good mineral spirits solubility is observed despite the high metal-to-acid ratios, and the product complexes seem very stable to heat as compared to the known class of overbased copper carboxylates.

In these copper complexes, the oxide core of CuO crystallite is triclinic, with again associated solubilizing amorphous organic material, especially of the metal hydroxyl carboxylate form. Freezing point depression in trichlorobenzene indicates average molecular weight on the order of 1,000+100, and in carbon tetrachloride by gel permeation chromatography, molecule sizes of 100 to 1,000Å and larger are observed. In the solid a uniform particle distribution of about 50 to 100Å core size is observed.

Iron Examples (Table IVa)

An iron complex is prepared as a mineral spirits solution product from the mixture of Example Fe-1 in Table IVa, by heating at about 115°–131° C. for about 10 hours, but here with continuous air introduction throughout, as well as continuous removal of water. The batch solution product after settling is filtered and then concentrated to a final product solution containing 17.9% iron. The solid product contains 26% iron.

In Example Fe-2, the procedure is similar to that of Fe-1, except that after the first 6 hours of air bubbling, during which the temperature is brought up to about 87° C. and held for about four hours, nitrogen is bubbled through the mixture for the remainder of the time while dehydration and concentration is carried out with the temperature being raised to about 156° C. The final liquid product contains 29.7% iron, or 67.7% solids with 43.9% iron.

From the diffraction and electron microscopy studies, the ultimate particles of the solid complex product appear to have an Fe$_3$O$_4$ spinel crystallite core similar to that of the manganese complexes, and the core is surrounded by larger amounts of the amorphous metal organic material. The ultimate particle cores are about 50 to 100Å, but the amorphous clusters of the ultimate particles are up to several hundred Angstroms in size. In trichlorobenzene, freezing point depressions indicate an average molecular weight of 800+100, while gel permeation chromatography in carbon tetrachloride indicates molecular sizes of 100 to 1,000Å and somewhat larger.

tures, e.g., about 210°–215° C. to complete the reaction. Accordingly, higher boiling diluents are required to be used in the reaction since mineral spirits will boil off. These higher boiling diluents may include various types and grades of hydrocarbon oils, both natural and synthetic. Generally it is preferred to use a mixture of mineral spirits and a higher boiling diluent oil to maintain fluidity. It is possible, of course, to use only mineral spirits and conduct the reaction at an elevated pressure, but this requires more expensive apparatus.

Sufficient nickel must be incorporated into the reaction mixture to provide complexes containing the desired quantity of metal in solution. An excess of nickel can be used to increase the speed of the reaction, and any unreacted nickel can be removed from the solution product by filtration.

Example Ni-1

A nickel complex is prepared as a mineral spirits and lubricating oil solution product from the mixture of Example Ni-1 in Table IVa by bubbling air through the mixture heated to a temperature of about 90° C. over a period of about 22 hrs. A portion of the NH$_4$OH (32 g) is added when the heat is applied followed by the potassium iodide. Other portions (10 g each) of the ammonium hydroxide are added after eight and ten hours of heating when the temperature of the reaction mixture is about 90° C. The nickel content of the solution at this time is about 15.7%.

The flow of air is stopped and replaced by a flow of nitrogen through the reaction mixture. Water is removed from the reaction mixture as the temperature is raised to about 210° C. over a period of about 16 hours. Some of the oil (100 g) is added to replace the water and TABLE IVa

| RAW MATERIAL | Ex. Fe-1 Bt. | Fe-1 Moles | Ex. Fe-2 Bt. | Fe-2 Moles | Ex. Ni-1 Bt. | Ex. Ni-2 Bt. |
|---|---|---|---|---|---|---|
| 2-ethylhexoic acid | 29 | 0.20 | — | — | 55.1 | 41.8 |
| neodecanoic acid | 127 | 0.70 | 158 | 0.90 | 73.1 | 16.7 |
| propionic acid | 22 | 0.30 | 30 | 0.40 | 24.4 | 8.4 |
| stearic acid | 58 | 0.20 | 85 | 0.30 | 55.1 | 25.1 |
| naphthenic acid | 70 | 0.20 | — | — | — | — |
| amyl ac. phosphate | 12 | 0.20(1) | 50 | 0.40 | (1) | —(2) |
| other org. (3) 10 | (4) — | — | | | | |
| (5) — | — | | | | | |
| total org. acids | 328 | 2.0 | 323 | 2.0 | — | — |
| Cellosolve | 270 | 3.0 | 135 | 1.5 | — | — |
| mineral spirits | 1400 | — | 1700 | — | — | — |
| oil | — | — | — | — | 897 | 1938 |
| water | 20 | — | 250 | — | 870 (4) | 357 (5) |
| 35% hydrazine | — | — | 10 | — | — | — |
| Eastazone | 8 | — | — | — | — | — |
| triethanolamine | — | — | 30 | — | — | — |
| NH$_4$OH | — | — | 130 | — | 334 | 143 |
| amyl alc. mix. isom. | — | — | (5 | —) (3) | — | — |
| potassium iodide | — | — | — | — | 7.7 | 3.4 |
| metal | 400 | 7.16 | 700 | 12.5 | 450 | 570 |
| air-tot. cu. ft. | yes | — | 27 | — | yes | yes |

(1) acetic acid; (2) formic acid; (3) glycerol; (4) mixture contained 55.1 Triton X-45;
(5) mixture contained 12.2 Texanol

| PRODUCT | | | | | | |
|---|---|---|---|---|---|---|
| Metal % | | 17.85 | | 29.7 | 28.1 | 51.4 |
| M/A ratio-moles | | — | | 4.0 | 3.7 | 15.4 |
| Met. conversion % | | — | | — | — | — |
| Non-volatile % | | 68.6 | | 67.7 | | |
| ACTIVE COMPONENT | | | | | | |
| Metal % | | 26.0% Fe | | 43.9% Fe | | |

Nickel Examples (Table IVa)

Nickel complexes can be prepared by a process similar to those described above. One difference is that the reaction mixtures must be heated to higher temperatures mineral spirits removed during the heating. The reaction product is filtered and the filtrate contains 28.1% nickel and a metal to acid mole ratio of 3.7.

Example Ni-2

The mixture of Ni-2 in Table IVa is prepared and air is bubbled through the mixture at 5 CFH as the mixture is heated to a temperature of about 90° C. over a period of about 30 hours. The air is replaced by nitrogen and the temperature of the mixture is raised to about 210° C. over a period of about four hours and maintained at about 200°-210° C. for four additional hours. The reaction solution is filtered, and product is found to contain 51.4% nickel with a metal to acid mole ratio of 15.4. The oil solution product containing 51.4% exhibits good solubility characteristics in mineral spirits, oil and xylene.

BIMETALLIC COMPLEXES

Polymetallic complexes are also similarly producible utilizing plural metal sources in the reaction batch as exemplified for the metal pairs manganese and zinc, manganese and barium, manganese and cobalt, set forth in Examples M-1, M-2, and M-3 respectively of Table V.

In Example M-1, all the materials including zinc oxide are admixed, excepting the manganese oxide and hydrazine, and heated to about 72° C., when the latter two components are successively added. The mixture is heated up to 126° C. to complete the reaction of the manganese oxide, and then air blowing is begun, with simultaneous dewatering and concentration as mineral spirits and water are removed. The batch is subjected to the air blowing until the solution is clear and then filtered.

The filtrate product has the indicated high total metal content of 39.4% and a metal to acid mole ratio of 9.1 with retained solublity. By diffraction and electron study as with prior examples, the dried products again exhibit the previously described oxide crystallite-cord and matrix type structure in the ultimate solution-dispersed particles, with both metals present in the core. The core is essentially of the spinel structure.

In Example M-2, the batch ingredients and procedure are similar to Example M-1, except for the use of the barium monohydrate. After all the barium hydroxide reacts quickly within a few minutes, the manganous oxide and hydrazine are successively added and heating begun to obtain substantially complete oxide reaction even below 98° C. After some initial higher heating to 134° C. to begin dehydration, the air blowing is initiated and continued at somewhat lower temperatures until the solution becomes clear, with simultaneous further dewatering and concentration. The final batch liquid is filtered.

The filtrate product is similar to that of Example M-1 in high metal content and M/A ratio with excellent hydrocarbon solubility. The ultimate "particle" structure contains atoms of barium as well as manganese in the core crystallite which is basically of a spinel structure.

In Example M-3, the ingredients of the first column comprising substantially all of the acids and the cobalt powder are charged into the reactor and air bubbling is begun with heating to about 71° C. for four hours. Thereafter the ingredients of the second column are added, first the manganous oxide slurried in the Cellosolve and water, the hydrazine and as reheating is progressing, the propionic acid. The heating is continued up to 97.5° C., until complete reaction of the oxide, and then dehydration at higher temperature is begun, followed by the air blowing again until clear. During the latter heating, water is removed from the mixture. The clear solution is filtered.

The filtered product has the indicated high metal content of about 40.0%, 58.1% (43.7% Mn + 14.4% Co) in the solid and a M/A mole ratio of about 6.7 with good solubility. The product has the spinel crystallite-cored particle structure, and some of the cobalt atoms in

TABLE V

| RAW MATERIAL | Ex. M-1 Bt. | Moles | Ex. M-2 Bt. | Moles | Ex. M-3 Bt. | Moles | Bt. | Moles |
|---|---|---|---|---|---|---|---|---|
| 2-ethylhexoic acid | 43 | 0.30 | 43 | 0.30 | — | — | — | — |
| neodecanoic acid | 36 | 0.20 | 36 | 0.20 | 99 | 0.55 | — | — |
| dodecyl benzene sulfonic acid | 15 | 0.05 | 15 | 0.05 | — | — | — | — |
| stearic acid | 43 | 0.15 | 43 | 0.15 | 43 | 0.15 | — | — |
| naphthenic acid | 34 | 0.10 | 34 | 0.10 | — | — | — | — |
| butyric acid | 18 | 0.20 | 18 | 0.20 | — | — | — | — |
| propionic acid | — | — | — | — | 23 | 0.30 | 7.5 | 0.10 |
| total org. acids | 189 | 1.00 | 189 | 1.00 | | | 172.5 | 1.10 |
| Cellosolve (*Acetate) | 54* | 0.40 | 54* | 0.40 | 20 | 0.22 | 90 | 1.00 |
| Mineral spirits | 1600 | — | 1600 | — | 1800 | — | 100 | — |
| water | 240 | — | 240 | — | 400 | — | 200 | — |
| hydrazine hydrate | 8 | — | 8 | — | — | — | 5 | — |
| zinc oxide | 41 | 0.62 | | | | | | |
| manganous oxide | 606 | 8.50 | 624 | 8.75 | — | — | 515 | 7.27 |
| barium monohydrate | — | — | 50 | 0.25 | — | — | — | — |
| Co Metal powder | — | — | — | — | 760 | — | — | — |
| triethanolamine | — | — | — | — | 6 | — | — | — |
| NH4OH | — | — | — | — | 60 | — | — | — |
| Air-total cubic feet | 7 | — | 7 | — | 9 | — | 12.3 | — |
| PRODUCT | | | | | | | | |
| Mn % | 36.7 | | 38.3 | | 30.1 | | | |
| Other metal % | 2.7 Zn | | 2.9 Ba | | 9.9 Co | | | |
| M/A Ratio (Molar) | 9.1 | | 9.0 | | 6.7 | | | |
| Mn Conversion % | 94.0 | | 94.1 | | | | | |
| Non-volatile % | 67.8 | | 67.4 | | 69.1 | | | |
| ACTIVE COMPONENT | | | | | | | | |
| Metals % | 58.1 (Mn + Zn) 3.9 Zn | | 61.0 (Mn + Ba) 4.3 Ba | | 58.1 (Mn + Co) 14.4 Co | | | | the core appear to be substituted for certain manganese atoms.

The embodiments of the invention in which an exclusive property or privilege is claimed are defined as follows:

1. An oil-soluble and hydrocarbon-soluble overbased transition metal organic composition consisting essentially of a metal oxide and a hydroxyl-metal-carboxylate or -sulfonate complex wherein the metal content which comprises at least one metal which is a transitional metal is in chemical combination partly with oxygen in a polynuclear metal oxide crystallite core and partly with at least two different aliphatic or alicyclic monocarboxylic acids or a mixture of one or more aliphatic or alicyclic monocarboxylic and aliphatic or aromatic monosulfonic acids containing at least two carbon atoms as hydroxyl-metal-carboxylate and hydroxy-metal-sulfonate groups, at least one of the acids being a monocarboxylic acid containing at least seven carbon atoms, and when the second acid is also a monocarboxylic acid, the second acid contains a number of carbon atoms in its longest chain differing by at least two carbon atoms from the total number of carbon atoms in the other, at least a portion of the carboxylate and sulfonate groups being hydrogen bonded to oxygen atoms of the core, and the remainder of the carboxylate and sulfonate groups are unbonded and in equilibrium with the bonded groups, and the ratio of total metal moles to the total moles of organic acid is greater than one.

2. A composition as described in claim 1 having a minimum average molecular weight in non-dissociating solvents of about 10,000.

3. A composition as described in claim 1 having an apparent minimum average molecular weight in dissociating solvents of about 1,000.

4. A composition as described in claim 1 wherein the metal atoms in the core consist of transitional metal atoms.

5. A composition as described in claim 1 representable by the empirical formula

$$[(ML_a)_b \cdot (HO-M-R_1)_c \cdot (HO-M-R_2)_d]_f$$

wherein
M is a metal atom with valence greater than one, is a transitional metal in the majority of metal occurrences in the composition, and each M may represent different metals;
L is an oxygen or a hydroxyl group;
$R_1$ is an organic monocarboxylate group;
$R_2$ is an organic monocarboxylate or monosulfonate group;
a is from about one to two;
b is greater than one;
c and d are each greater than zero; and c+d is at least three; and
f is at least one.

6. A composition as described in claim 1 wherein said crystallite core, considered nominally in terms of dimensions of a cube, has an edge length on the order of 50 to 100Å.

7. A composition as described in claim 1 including a plurality of metals.

8. A composition as described in claim 1 wherein the metal consists of copper or a metal from the first transitional series.

9. A composition as described in claim 8 wherein the metal is manganese, cobalt, iron, copper or nickel.

10. A composition as described in claim 9 wherein the metal is cobalt.

11. A composition as described in claim 9 wherein the metal is iron.

12. A composition as described in claim 9 wherein the metal is copper.

13. A composition as described in claim 9 wherein the metal is manganese.

14. A composition as described in claim 9 wherein the metal is manganese present in the divalent and trivalent states.

15. A composition as described in claim 14 wherein trivalent manganese constitutes about 67% of the total manganese content.

16. A composition as described in claim 9 wherein the metal is iron present in the divalent and trivalent states.

17. A composition as described in claim 9 wherein the metal is nickel.

18. A composition as described in claim 1 wherein the two acids are carboxylic acids which differ from each other by at least six carbon atoms.

19. A composition as described in claim 1 wherein the mole ratio is at least 2.

20. A composition as described in claim 1 wherein a portion of the metal is in combination with one or more alkoxy alkanols as hydroxy-metal-alkanolate groups.

21. A method for preparing oil-soluble and hydrocarbon-soluble highly overbased mangano-organic compositions which comprises the steps of (a) providing a mixture comprising an acid soluble manganese compound, water, a diluent and a mixture of at least two different aliphatic or alicyclic monocarboxylic acids or a mixture of one or more aliphatic or alicyclic carboxylic and aliphatic or aromatic monosulfonic acids containing at least two carbon atoms, wherein at least one of the acids of the mixture is a monocarboxylic acid containing at least seven carbon atoms, and when the second acid is also a monocarboxylic acid, the second acid contains a number of carbon atoms in its longest chain differing by at least two carbon atoms from the total number of carbon atoms in the other, the mole ratio of manganese to total moles of organic acid in the mixture being greater than 1, (b) heating the mixture to initiate an exothermic reaction, (c) maintaining the mixture at an elevated temperature and under sufficient pressure to prevent substantial volatilization of the water present until the desired manganese content or a substantially constant maximum reacted manganese content is obtained, (d) removing substantially all of the free water from the mixture, (e) treating the heated mixture with oxygen to oxidize the mixture, and (f) recovering the overbased composition as a solution in the diluent.

22. The method of claim 21 wherein the temperature of the mixture in step (c) is maintained between about 60° C. and 100° C.

23. The method of claim 21 wherein oxygen is bubbled through the mixture in step (e) at a temperature of about 110°–150° C. until no further water can be distilled from the reaction mixture and the mixture is substantially homogeneous.

24. The method of claim 21 wherein the reaction mixture is maintained in an inert atmosphere in steps (a), (b) and (c).

25. The method of claim 21 wherein the mixture provided in step (a) contains manganese oxide as the only metal compound.

26. The method of claim 25 wherein other metal oxides are included in the mixture of step (a) and a mixed metal composition is obtained.

27. A method of preparing oil-soluble and hydrocarbon-soluble overbased organo manganese, cobalt, iron, copper and nickel compositions which comprises the steps of
   (a) providing a mixture containing
      (i) as a metal source, cuprous oxide, a metal selected from the group consisting of manganese, cobalt, iron, copper and nickel, mixtures thereof, or mixtures thereof with other metals,
      (ii) an organic acid mixture comprising at least two different aliphatic or alicyclic monocarboxylic acids or one or more aliphatic or alicyclic monocarboxylic acids and aliphatic or aromatic monosulfonic acids containing at least two carbon atoms, at least one of the acids being a monocarboxylic acid containing at least seven carbon atoms, and when the second acid also is a monocarboxylic acid, the second acid contains a number of carbon atoms in its longest chain, differing by at least two carbon atoms from the total number of carbon atoms in the other,
      (iii) water, and
      (iv) a diluent, and wherein the ratio of total metal moles to total moles of acid is greater than 1;
   (b) treating the mixture with oxygen while maintaining the mixture at the reflux temperature until a desired soluble metal content is obtained,
   (c) dehydrating the reaction mixture until substantially all of the water is removed, and
   (d) recovering the product as a solution in the diluent.

28. The method of claim 27 wherein the metal source is nickel powder and the mixture obtained from step (b) is heated to a temperature of up to about 210° C. in a nitrogen atmosphere and mainained at this temperature prior to dehydration until the desired metal content or a substantially constant maximum soluble nickel content is obtained.

29. The method of claim 27 wherein the metal source is cuprous oxide and steps (b) and (c) occur simultaneously.

30. The method of claim 27 wherein the reaction mixture is dehydrated in step (c) under an inert atmosphere.

* * * * *